(12) United States Patent
Rocha-Singh

(10) Patent No.: US 10,881,541 B1
(45) Date of Patent: Jan. 5, 2021

(54) SYSTEMS AND METHODS FOR TREATING VENOUS COMPRESSION/OBSTRUCTION SYNDROMES

(71) Applicant: Krishna Rocha-Singh, Springfield, IL (US)

(72) Inventor: Krishna Rocha-Singh, Springfield, IL (US)

( * ) Notice: Subject to any disclaimer, the term of this patent is extended or adjusted under 35 U.S.C. 154(b) by 0 days.

(21) Appl. No.: 16/865,154

(22) Filed: May 1, 2020

(51) Int. Cl.
  *A61F 2/915* (2013.01)
  *A61F 2/958* (2013.01)
  *A61F 2/966* (2013.01)
  *A61B 6/00* (2006.01)
  *A61B 6/03* (2006.01)
  *A61B 5/026* (2006.01)

(52) U.S. Cl.
  CPC .............. *A61F 2/915* (2013.01); *A61F 2/958* (2013.01); *A61F 2/966* (2013.01); *A61B 5/0263* (2013.01); *A61B 6/032* (2013.01); *A61B 6/504* (2013.01); *A61B 6/507* (2013.01); *A61F 2002/91575* (2013.01); *A61F 2250/0098* (2013.01)

(58) Field of Classification Search
  CPC . A61B 6/504; A61B 6/507; A61F 2/86; A61F 2/90; A61F 2/915; A61F 2/95; A61F 2/958; A61F 2/962; A61F 2/966; A61F 2002/825; A61F 2002/91508; A61F 2002/91516; A61F 2002/91525; A61F 2250/0018; A61F 2250/0098
  See application file for complete search history.

(56) References Cited

U.S. PATENT DOCUMENTS

| | | | |
|---|---|---|---|
| 5,354,309 A | 10/1994 | Schnepp-Pesch et al. | |
| 5,938,697 A | 8/1999 | Killion et al. | |
| 5,951,599 A * | 9/1999 | McCrory | A61B 17/12022 606/108 |
| 5,954,765 A | 9/1999 | Ruiz et al. | |
| 6,059,822 A | 5/2000 | Kanesaka et al. | |
| 6,231,597 B1 | 5/2001 | Deem et al. | |
| 6,468,302 B2 | 10/2002 | Cox et al. | |
| 6,610,087 B1 | 8/2003 | Zarbatany et al. | |
| 6,613,074 B1 * | 9/2003 | Mitelberg | A61B 17/12022 606/200 |
| 6,899,729 B1 * | 5/2005 | Cox | A61F 2/915 606/200 |
| 7,258,697 B1 * | 8/2007 | Cox | A61F 2/91 623/1.14 |
| 7,658,759 B2 * | 2/2010 | Case | A61F 2/2475 623/1.15 |

(Continued)

OTHER PUBLICATIONS

Graaf, et al., Iliocaval Confluence Stenting for Chronic Venous Obstructions, Cardiovasc. Intervent Radiol. 38:1198-1204 (2015).

(Continued)

*Primary Examiner* — Ryan J. Severson
(74) *Attorney, Agent, or Firm* — Eversheds Sutherland (US) LLP; Christopher C. Bolten; Nicola A. Pisano

(57) ABSTRACT

Apparatus and methods are provided for treating patients exhibiting symptoms of hypertension, isolated systolic hypertension, heart failure with preserved ejection fraction, May-Thuner Syndrome or dyspnea by diagnosing and reducing narrowing of a patient's iliac vein caused by extrinsic localized compression using a stent having circumferential differential radial stiffness and delivery catheter for aligning and deploying such stents.

10 Claims, 6 Drawing Sheets

(56) References Cited

U.S. PATENT DOCUMENTS

| | | | |
|---|---|---|---|
| 8,475,518 B2 * | 7/2013 | Cox | A61F 2/91 623/1.15 |
| 8,702,744 B2 * | 4/2014 | Bates | A61F 2/95 606/192 |
| 9,750,603 B2 | 9/2017 | Bell et al. | |
| 10,271,977 B2 * | 4/2019 | Longo | A61F 2/91 |
| 10,357,386 B2 * | 7/2019 | Schaeffer | A61F 2/856 |
| 10,398,421 B2 * | 9/2019 | Celermajer | A61B 17/02 |
| 10,512,556 B2 * | 12/2019 | Longo | A61F 2/915 |
| 10,588,764 B2 * | 3/2020 | Longo | A61F 2/07 |
| 10,610,669 B2 * | 4/2020 | Rocha-Singh | A61M 25/0194 |
| 10,624,621 B2 * | 4/2020 | Celermajer | A61F 2/06 |
| 10,675,163 B2 * | 6/2020 | Schaeffer | A61F 2/915 |
| 10,695,201 B2 * | 6/2020 | Feng | A61F 2/91 |
| 2002/0099406 A1 * | 7/2002 | St. Germain | A61F 2/90 606/198 |
| 2005/0049678 A1 * | 3/2005 | Cocks | A61F 2/91 623/1.15 |
| 2010/0057192 A1 * | 3/2010 | Celermajer | A61F 2/2412 623/1.26 |
| 2014/0257167 A1 * | 9/2014 | Celermajer | A61F 2/24 604/9 |
| 2014/0378890 A1 * | 12/2014 | Rocha-Singh | A61N 7/00 604/21 |
| 2017/0266411 A1 * | 9/2017 | Rocha-Singh | A61M 25/0074 |
| 2017/0266414 A1 * | 9/2017 | Rocha-Singh | A61M 25/04 |
| 2018/0168833 A1 * | 6/2018 | Feng | A61F 2/915 |
| 2019/0076276 A1 * | 3/2019 | Longo | A61F 2/89 |
| 2019/0076278 A1 * | 3/2019 | Longo | A61F 2/91 |
| 2019/0247208 A1 * | 8/2019 | Longo | A61F 2/07 |
| 2019/0247209 A1 * | 8/2019 | Longo | B24B 5/22 |
| 2020/0188148 A1 * | 6/2020 | Longo | A61F 2/07 |
| 2020/0245991 A1 * | 8/2020 | Celermajer | A61F 2/2442 |

OTHER PUBLICATIONS

VENOVO® Venous Stent System, Instructions for Use, Bard Peripheral Vascular, Aug. 2018 (11 pages).

Vici Venous Stent® System, STE-IFU-0905 Rev A, Instructions for Use, Boston Scientific Corporation (2019) (36 pages).

Lobo et al., Central Iliac Arteriovenous Anastomosis for Uncontrolled Hypertension, Hypertension, 70:1099-1105 (2017).

May, R. and Thurner, J., The Cause of the Predominantly Sinistral Occurrence of Thrombosis of the Pelvic Veins, Angiology, 8(5):419-27 (1957).

* cited by examiner

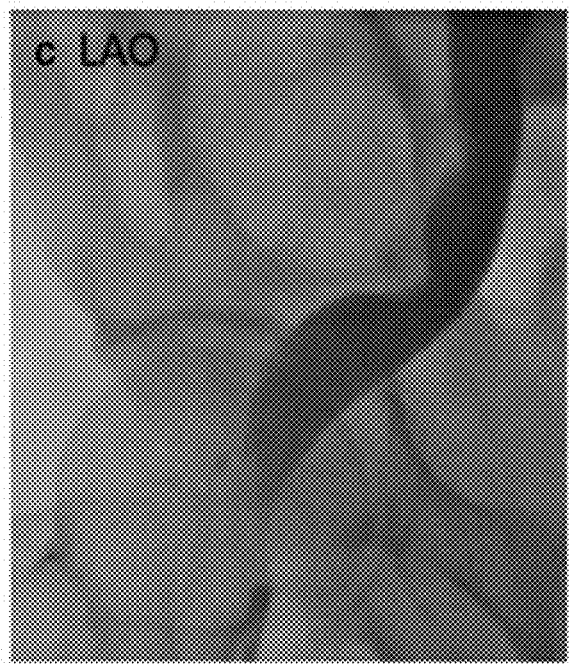
FIG. 4A  FIG. 4B
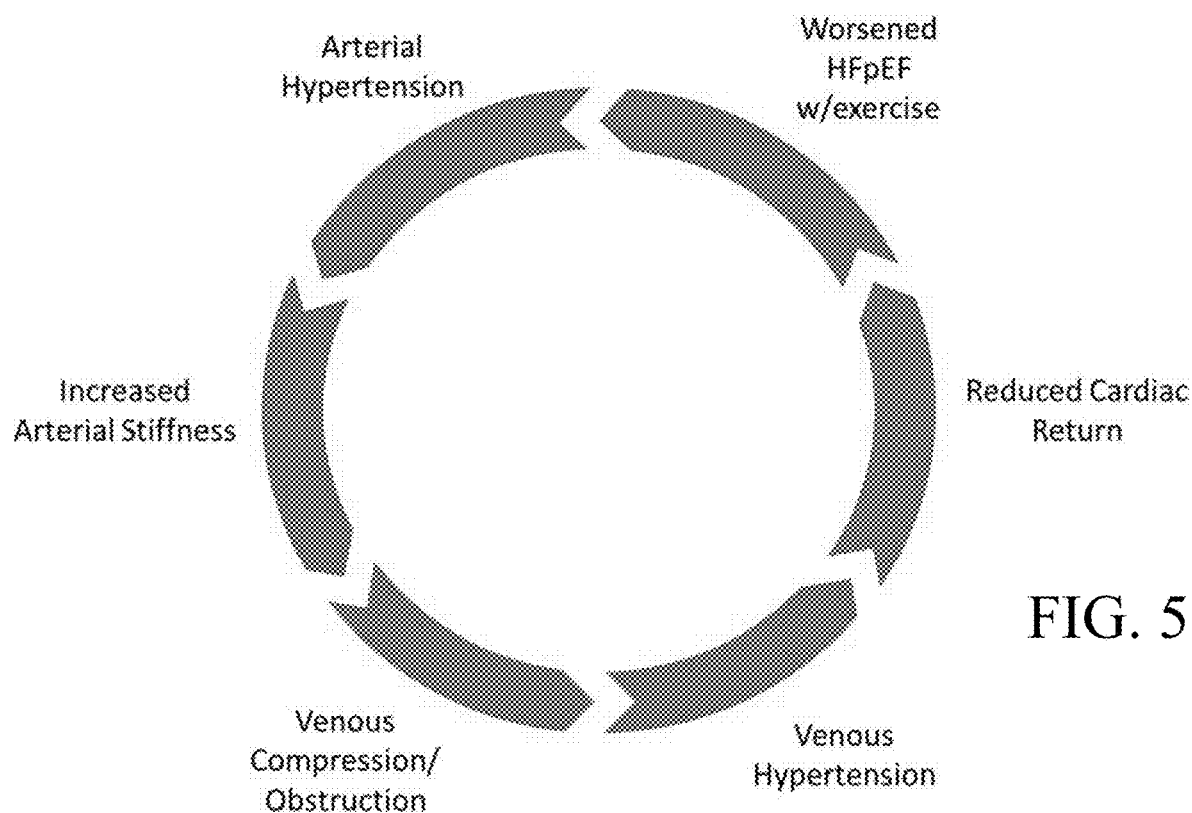
FIG. 5

SYSTEMS AND METHODS FOR TREATING VENOUS COMPRESSION/OBSTRUCTION SYNDROMES

This application relates generally to devices and methods for reducing venous compression/obstruction arising from localized extrinsic loads, and thereby, to provide relief from a number of cardiovascular ailments hypothesized to arise therefrom.

BACKGROUND

Hypertension is a disease that affects more than 77.9 million adults in the United States and approximately one billion individuals worldwide. In 2008, elevated blood pressure (BP) affected approximately 40% of adults 25 years of age or greater globally. According to a 2014 report from the American Heart Association (AHA), based on NHANES/NCHS data through 2010, one in three adults has high BP, and 74.9% of these subjects are undergoing treatment for hypertension. The AHA further reported that hypertension is under control in only 53% of these patients.

Recently, the Eighth Report of the Joint National Committee (JNC 8) reduced target BP recommendations and suggested that the treatment goal for the hypertensive population ≥60 years of age should be <150/90 mmHg, and <140/90 mmHg for the younger than 60 year hypertensive population, and hypertensive adults (all ages) with diabetes or non-diabetic chronic kidney disease (CKD). These recommendations do not suggest that there is no benefit of further pressure reduction, but explicitly recognize that current drug strategies have failed to demonstrate benefit.

Hypertension remains a major cause of morbidity and mortality worldwide, and is associated with coronary heart disease, stroke, chronic kidney disease, and heart failure. Worldwide, hypertension is the primary cause of death and disability (WHO, 2013). Failure to comply with lifelong antihypertensive poly-pharmacy results in these rates of morbidity and mortality. Isolated systolic hypertension (ISH) (defined as SBP ≥160 mmHg and DBP <95 mmHg), is another hypertensive illness of growing epidemiologic importance because it correlates with an aging population demographic and may reflect as an underlying cause age-related loss of aortic and arterial compliance. Systolic blood pressure may be largely dependent on an increase in arterial stiffness caused by structural age-related vascular changes. Currently available antihypertensives, such as vasodilators that act primarily on vessel resistance, have been observed to have only limited effect on arterial stiffness.

The ROX HTN-1 study was a prospective, single-arm, open label, multicenter study designed to evaluate the safety and effectiveness of the ROX Anastomotic Coupler System in lowering blood pressure in subjects with severe hypertension, particularly patients with ISH. M. D. Lobo et al., "Central Iliac Arteriovenous Anastomosis for Uncontrolled Hypertension," Hypertension 70:1099-1105 (2017). In that study, a nitinol coupler was used to create an arteriovenous anastomosis in a central iliac artery, which anastomosis relieved elevated pressure in the iliac artery and reduced hypertension. The clinical results of the study indicated that creation of an arteriovenous side-to-side anastomosis with the ROX Coupler could be performed safely and lowered blood pressure in severe, resistant hypertensive subjects.

The follow-up ROX HTN-2 Study was a prospective, randomized, open-label, multicenter, US-based study to evaluate the safety and effectiveness of the ROX Coupler in subjects with severe, treatment resistant hypertension. Although there were no documented procedure related safety concerns, follow-up from the ROX HTN1 study and one patient in the ROX HTN2 treatment arm noted the occurrence of new venous stenoses, either at or above the Coupler device site, occurring between 6-12 months post-Coupler implantation. The occurrence of the venous stenosis was associated with ipsilateral limb swelling and return of severe hypertension, both of which resolved after the implantation of a venous nitinol stent to resolve the stenosis.

Creation of an arteriovenous anastomosis, as in ROX HTN trials, is believed to provide a purely mechanical reduction in BP that is likely unrelated to either reduction of neurosympathetic or hormonal activity. Investigators have observed that arteriovenous fistula formation in pre-dialysis patients resulted in persistent reductions in arterial stiffness, as demonstrated by reductions in carotid femoral pulse wave velocity (CF-PWV) and aortic augmentation index (AI) and reduced BP.

Heart failure with preserved ejection fraction (HFpEF) is characterized by a normal left ventricular ejection fraction (EF), increased left ventricular stiffness and abnormal ventricular relaxation. The combination of increased left ventricle stiffness and ventricular relaxation during diastole results in impaired filling and increased left intraventricular end-diastolic pressure. The primary clinical manifestation of HFpEF is shortness of breath with exertion, effort related fatigue and a marked reduction of exercise tolerance/capacity. However, while at rest, most HFpEF patients have no symptoms.

A recent observation is the contribution of reduced venous filling to the right heart to exertional symptoms in HFpEF patients. This reduction in cardiac venous filling (e.g., cardiac preload) can be caused by various venous compression, particularly in the pelvis. Compression of pelvic veins can be caused by inherent anatomic features (i.e., an overriding artery, ligaments) obesity or uterine fibroids. May-Thurner Syndrome (MTS), reported in R. May and R. J. Thurner, "The cause of the predominantly sinistral occurrence of thrombosis of the pelvic veins," Angiology, 8(5):419-27 (1957), arises from compression of the left common iliac vein by the right common iliac artery, usually at the level of the L5 vertebrae. The resultant compression of the vein by arterial pulsations against the lumbar vertebrae and chronic irritation of the venous endothelium led May and Thurner to theorize that cyclical venous compression and the resultant venous gradient were an underlying cause of left iliac venous thrombosis.

Venous compression, unlike a venous stenosis, tends to be dynamic, asymmetric and may worsen during states of increased cardiac output requirements, including exertion/exercise. Under such conditions, significant venous outflow obstruction may occur, reducing venous return to the right heart, which in turn may cause a decrease in cardiac output and development of dyspnea. Patients presenting with such symptoms frequently are given a diagnosis of heart failure with preserved ejection fraction (HFpEF). Of interest, the association between May-Thurner venous compression and HFpEF in females has a 30-40% higher prevalence than age-matched controls.

Further, an increase in arterial calcification and stiffness, associated with increasing age and diabetes, may be an important contributor to arterial compression of the vein, especially in the ilio-caval circulation.

In view of the foregoing, it would be desirable to provide methods and devices that treat various venous compression/obstruction syndromes that reduce venous return to the right heart and thereby impact the functional capacity of patients with HFpEF and result in markedly diminished quality of life due to debilitating fatigue and exertional shortness of breath.

SUMMARY OF THE INVENTION

It is the inventor's insight that many illnesses, including MTS, HFpEF and the resulting dyspnea, have as a root cause localized narrowing of the iliac veins caused by compression or obstruction. In particular, it is hypothesized that the foregoing syndromes result or may be exacerbated by extrinsic localized venous compression/obstruction arising from several sources. Such sources of compression/obstruction may be intermittent or continuous, asymmetric, and may include an artery overlying a patient's iliac vein that has age-related reduction in arterial compliance. Such compression also may arise due to exercise or an overriding ligament or bone, or an acquired complication such as uterine fibroids that may cause compression of the patient's iliac veins. It is further hypothesized that venous compression/obstruction reduces blood return to the heart, which in turn may reduce oxygenation in the lungs, and further result in the left heart working harder to maintain sufficient blood pressure. Moreover, the increased venous pressure in the extremities resulting from the venous compression also is believed to increases the arterial pressure, resulting in increased systolic pressure, hypertension and HFpEF.

In accordance with the principles of the present invention, apparatus and methods are provided for reducing venous compression and obstruction, which expected to improve venous return flow in the lower extremities and reduce the cardiac work required to maintain adequate blood flow. In one preferred embodiment, stents configured for stenting the iliac veins are provided, wherein the stents have variable circumferential stiffness. In particular, such stents include a circumferential portion, suitable for alignment with an overriding artery, ligament or bone that counteracts an extrinsic compressive force. Such circumferential variability in stiffness may be achieved by varying strut thicknesses, geometries, lengths and/or widths around the stent circumference to address the asymmetric nature of applied loads. For example, the stent may have differential radial stiffness disposed over a range of between one-half and one-quarter of the stent circumference. The stent may be formed of a laser-cut metal or metal alloy tube and feature an open cell or closed cell geometry, and may be either self-expanding or balloon expandable. As a further alternative, the inventive stent may comprise a woven or braided material. In addition, the radial stiffness of the inventive stents may vary along a longitudinal direction of the stent. Advantageously, employing variable circumferential stiffness is expected to provide increased longitudinal flexibility to facilitate stent placement, to enhance fracture resistance, and to reduce the risk of potential stenosis.

In accordance with another aspect of the invention, delivery catheters are provided that facilitate delivery and deployment of the inventive stents. In particular, the delivery catheters include features that enable the stent orientation relative to the overriding compressive artery, ligament or bone to be accurately determined prior to stent deployment. For example, the catheter may include a marker band system, arrayed circumferentially, that allows directional deployment of the stent under fluoroscopic guidance, to align a preferred portion of the differential radial strength and hoop strength against anatomical feature inducing the venous compression. Delivery catheters suitable for use with the stents of the present invention preferably are sufficiently flexible to negotiate tortuous venous anatomy. In addition, preferred delivery catheters also are sufficiently rigid to permit torque applied at the catheter handle to be transmitted to the distal region of the catheter, thereby to orient the directional features of the stent with the anatomical feature inducing the venous compression.

Methods of using the stents and delivery catheter of the present invention to treat HFpEF, exertional dyspnea and MTS are also provided.

BRIEF DESCRIPTION OF THE DRAWINGS

FIGS. 4A and 4B are, respectively, an anterior-posterior (AP) and left anterior oblique view venograms of a patient's external iliac vein showing extrinsic venous compression. The artery is not shown.

FIG. 5 is a schematic illustrating the inventive insight that venous compression may both arise from and contribute to a number of cardiovascular illnesses;

DETAILED DESCRIPTION OF THE INVENTION

Apparatus and methods of the present invention are designed to reduce or eliminate extrinsic compression/obstruction of the iliac veins, which is hypothesized to result in or contribute to a number of cardiovascular syndromes including hypertension, ISH, HFpEF, MTS and dyspnea. The foregoing syndromes may arise or be exacerbated by venous compression caused by a variety of anatomical conditions, such as an artery overlying a patient's iliac vein, due to exercise, an overriding ligament or bone, or an acquired complication such as uterine fibroids. For example, it is expected that due to age-related reduction in arterial compliance, an overlying artery may result in persistent compression of a patient's iliac vein, which may reduce venous return to the heart and in turn, reduce blood flow to and oxygenation in the lungs. These effects may in turn cause the left heart to work harder to maintain sufficient blood pressure and increase venous pressure in the extremities, thereby contributing to increases arterial pressure, increased systolic pressure, hypertension and apparent HFpEF.

To address the foregoing situation, the inventive apparatus and methods reduce extrinsic venous compression and obstruction, and are expected to improve venous return flow in the lower extremities, reduce venous hypertension, and reduce the cardiac work required to maintain adequate blood flow to the lungs.

Figure 1A:
FIGS. 1A and 1B are, respectively, a venogram of a venous stenosis located above a ROX Coupler as observed during follow-up from the ROX HTN-2 trial, and a venogram showing resolution of the venous stenosis post implantation of a conventional stent in the patient's iliac vein.

The inventor's insight that extrinsic venous compression/obstruction may contribute to the aforementioned syndromes is based in part on the results reported during the ROX HTN-1 and HTN-2 trials. As discussed above, the ROX Coupler was a nitinol device designed to mechanically treat hypertension by creating an arteriovenous fistula between a patient's iliac artery and iliac vein. Although there were no documented procedure-related safety concerns, follow-up from the ROX HTN1 study and one patient in the ROX HTN2 treatment arm noted the occurrence of new venous stenoses between 6-12 months post-coupler implantation, either at or above the Coupler device site. FIG. 1A is a venogram of such a venous stenosis located above a ROX Coupler, as observed during the follow-up period. Further evaluation of procedural angiograms and venograms noted a potential association of the venous stenosis and upstream compression of the external iliac vein by a non-compliant external iliac artery. This was a new observation, suggesting that the venous pressure gradient caused by the arterial compression of the vein may contribute to the development of the venous stenosis.

Figure 1B:
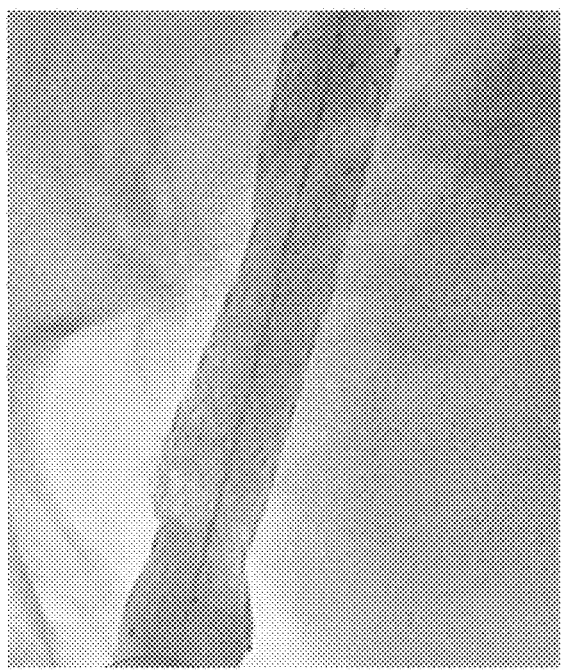

As depicted in FIG. 1A, the venogram shows significant narrowing in the iliac vein that is coupled to the iliac artery at a location just downstream of the anastomosis. Such venous stenoses were associated with recurrence of ipsilateral limb swelling and return of severe hypertension. The occurrence of a venous stenosis is theorized to result from increased blood turbulence across the fistula and the formation of a high-pressure arterial jet against the venous wall in the presence of an upstream venous compression caused by an overriding arterial segment. More specifically, the combined effects of platelet activation caused by barotrauma due to the pressure gradient across the anastomosis, together with abrupt reduction in flow velocity within the vein caused by the venous compression is hypothesized to lead to venous stenosis. Limb swelling and hypertension resolved after implantation of a conventional nitinol venous stent in the patient's iliac vein to resolve the stenosis, as depicted in FIG. 1B. Current stenting options include use of braided or laser cut nitinol stents to expand the venous vessels. Braided stents have good structural flexibility but are susceptible to stress-induced fracture when subjected to long-term use. Additionally, conventional stents provide uniform radial stiffness circumferentially even though the underlying venous compression is not.

Figure 2:
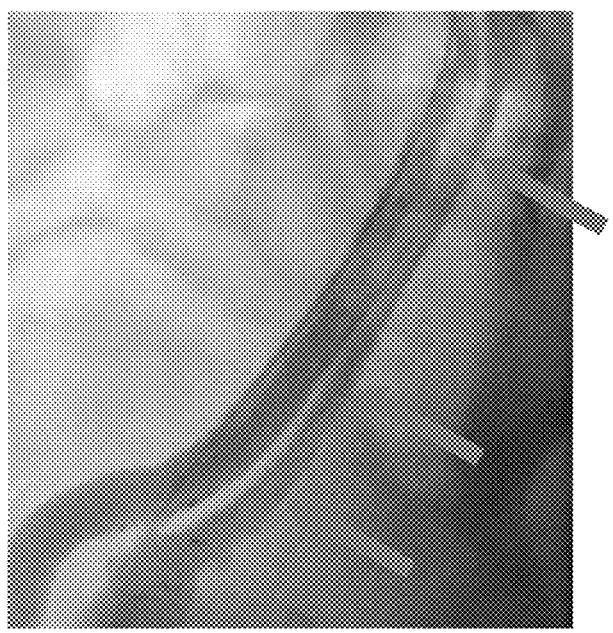
FIG. 2 is a venogram showing extrinsic compression of a patient's iliac vein by the external iliac artery above the placement site of a ROX Coupler.

FIG. 2 is a venogram of another patient's iliac region following implantation of a ROX Coupler to create an arteriovenous fistula to treat hypertension. As illustrated by the arrows in FIG. 2, simultaneous arterial and venous contrast injections showed significant compression of the iliac vein.

Figure 3:
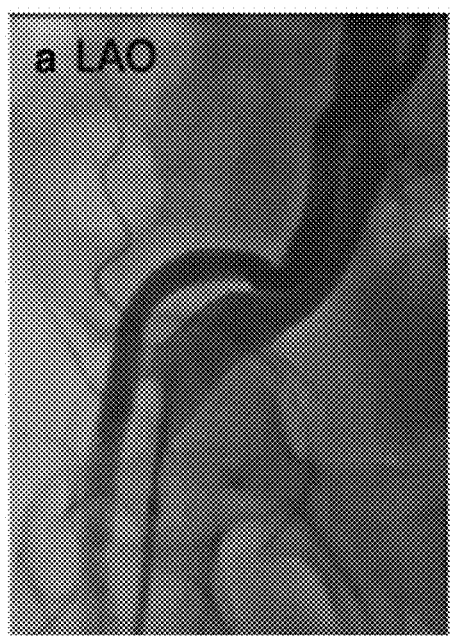
FIG. 3 is a venogram showing simultaneous arterial (lateral) and venous contrast injections in a patient with resistant hypertension, demonstrating compression of the vein by the overriding artery.

FIG. 3 is a venogram of another patient showing simultaneous arterial and venous contrast injections. This patient exhibited resistant hypertension, but had no symptoms of lower limb swelling. FIGS. 4A and 4B are, respectively, an anterior-posterior (AP) and left anterior oblique view venograms for the same patient. In this case, it is apparent that the localized extrinsic compression of the patient's iliac vein shown in FIGS. 4A and 4B results from the overriding arterial segment shown in FIG. 3. It is the inventor's insight, based on his review of the reported ROX coupler—venous stenosis experience as depicted in FIGS. 1-2 and the venous compression as observed in FIGS. 3-4, that other naturally occurring situations, such as age-related reduction of compliance of overriding arterial segments, exercise, an overriding ligament or bone or an acquired complication, such as uterine fibroids, may cause extrinsic iliac venous compression that manifests as venous hypertension, ISH, HFpEF, and venous compression syndrome with dyspnea. Notably, such venous compression may occur without limb swelling, and thus provide few clues for the clinician to diagnose venous compression as a cause or contributor to the patient's syndrome.

Referring to FIG. 5, it is the applicant's insight that iliac venous compression may arise from, or be a contributor to, a cycle of cardiovascular illnesses. Although there are many contributors to worsening symptoms of HFpEF, including for example, obesity, age, atrial fibrillation, it is hypothesized that venous compression/obstruction contributes to peripheral venous hypertension and impairs cardiac pre-load reserve, and thus HFpEF. The reduced supply of blood to the lungs may in turn result in lower oxygenation and increased left heart activity to maintain adequate blood flow. In addition, arterial hypertension, as well as other factors such as aging and obesity, may result in increased arterial stiffness, such that less compliant iliac arteries may impose additional extrinsic compressive forces on adjacent iliac veins. As described below, it is a goal of the systems and methods of the present invention to reduce venous compression and mitigate the downstream cardiovascular syndromes that may arise therefrom.

In accordance with one aspect of the present invention, a method of treating cardiovascular syndromes, including hypertension, ISH, HFpEF, MTS and dyspnea, is provided. In accordance with that method, a clinician assesses, and if present, ameliorates iliac vein compression for patients exhibiting symptoms of hypertension, ISH, HFpEF, MTS and dyspnea. Further in accordance with the invention, the clinician may employ various imaging modalities, including non-invasive magnetic resonance venography or computed tomography venography, to confirm whether the patient suffers from extrinsic iliac vein compression or obstruction, and if so, selects and implants a stent constructed in accordance with the principles of the invention.

Figure 6A:
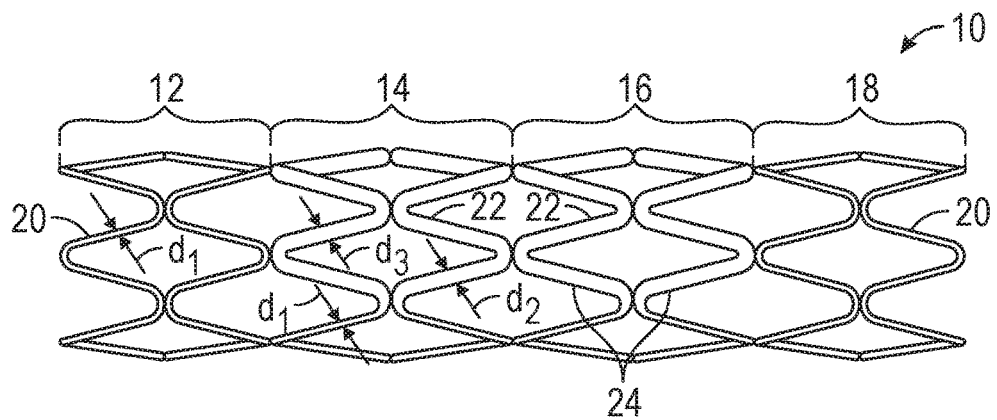
FIGS. 6A and 6B are, respectively, a side view and end view an embodiment of an exemplary stent constructed in accordance with the principles of the present invention.
Figure 6B:
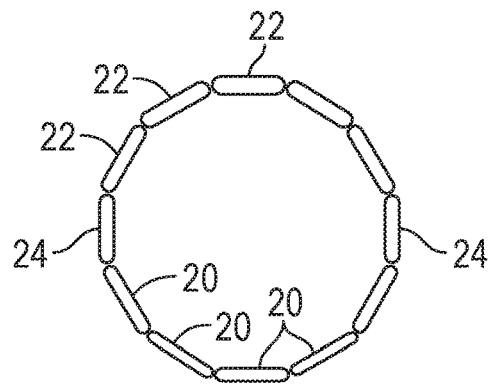

Referring now to FIGS. 6A and 6B, a first embodiment of a stent constructed in accordance with the principles of the present invention is described. Stent 10 has a variable circumferential stiffness, wherein a circumferential portion of the stent includes higher radial stiffness than adjoining portions, which portion may be aligned to resist compressive extrinsic forces applied by an overriding artery, ligament, tissue or bone. Stent 10 illustratively includes four longitudinal sections 12, 14, 16 and 18 comprising zig-zag struts, although more or fewer longitudinal sections may be employed during manufacture to make a stent of desired length.

Sections 12-18 of stent 10 illustratively are formed from struts 20, 22 and 24 that have multiple diameters. In particular, sections 12 and 18 are formed of struts 20 having diameter $d_1$, which also partly extend around the circumferences of sections 14 and 16. Sections 14 and 16 also include struts 22 having thickness $d_3$ extending over an arc of each section, and struts 24 of intermediate thickness $d_2$, which connect struts 20 and 24. As depicted in FIG. 6A, diameter $d_1$<diameter $d_2$<diameter $d_3$, such that the radial stiffness of sections 14 and 16 in the arc of the circumference having struts 22 and 24 is higher than the radial stiffness of the remaining circumference of those sections. In this manner, stent 10 provides a high radial force to counteract an asymmetric localized extrinsic compressive force, while applying lesser force around the remaining circumference of the stent. Advantageously, using thicker struts 22 and intermediate struts 24 only over an arc of the circumference allows the stent to remain longitudinally flexible, thereby allowing it to negotiate tortious anatomy during delivery to facilitate stent placement, to enhance fracture resistance, and to reduce the risk of potential stenosis.

FIG. 6B depicts stent 10 when viewed from one end. Struts 22 extend over approximately 40% (5/12) of the circumference of stent, stents 20 extend over approximately 40% (4/12) of the circumference, and struts 24 interconnect struts 20 and 22 over the remaining approximately 20% of the circumference. As will be understood by a person of skill in the art of stent design, the proportion of struts 20-24 may be adjusted to vary the arc of the zone of high radial stiffness. Depending upon the intended application, stent 10 may have differential radial forces distributed over from one-fourth or less, to half (½) or more of its circumference.

In addition to varying strut thicknesses, circumferential variability in stiffness may be achieved by altering the geometries, lengths and widths of struts around the stent circumference. Stent 10 may be formed of a laser-cut metal or metal alloy tube, and may be either self-expanding (e.g. nitinol) or balloon expandable (e.g. a cobalt chromium alloy). Alternatively, a stent constructed in accordance with the present invention may include an open cell or closed cell geometry, or may comprise a woven or braided material. As a further alternative or in addition, the radial stiffness of the inventive stents may vary along a longitudinal direction of the stent.

Figure 7:
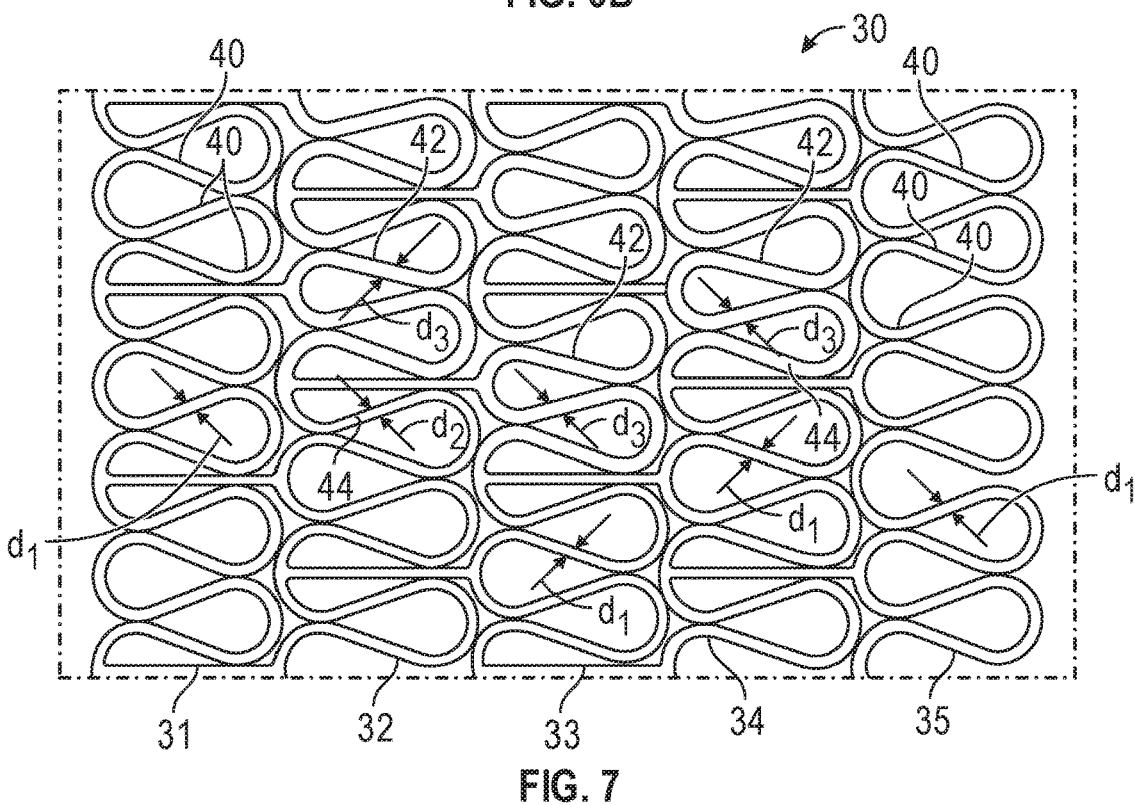
FIG. 7 is an alternative embodiment of an exemplary stent constructed in accordance with the principles of the present invention, wherein the stent is sliced open and flattened.

With respect to FIG. 7, an alternative stent constructed in accordance with the principles of the present invention is described. Stent 30 includes longitudinal sections 31, 32, 33, 34 and 35 comprising serpentine struts 40, 42 and 44 coupled by longitudinal struts 46. End sections 31 and 35 are formed of struts 40 having diameter $d_1$, which also partly extend around the circumferences of sections 32-34. Sections 32-34 also include struts 42 having thickness $d_3$ extending over an arc of each section, and struts 44 of intermediate thickness $d_2$, which connect struts 20 and 24. As depicted in FIG. 7, diameter $d_1$<diameter $d_2$<diameter $d_3$, such that the radial stiffness of sections 32, 33 and 34 in the arc of the circumference having struts 42 and 44 is higher than the radial stiffness of the remaining circumference of those sections. Stent 30 therefore provides a high radial force to counteract an asymmetric localized extrinsic compressive force, while applying lesser force around the remaining circumference of the stent. Use of struts 42 and struts 44 only over an arc of the circumference allows the stent to remain longitudinally flexible, thereby allowing it to negotiate tortious anatomy during delivery to facilitate stent placement and to enhance fracture resistance. In addition, the use of smaller diameter struts in areas where high radial stiffness is not required is expected to reduce the risk of potential stenosis.

In accordance with another aspect of the invention, delivery catheters are provided that facilitate delivery and deployment of the inventive stents to an ilio-caval compression site transvascularly. In particular, the delivery catheters suitable for use with the inventive stents include features that enable the stent to be accurately oriented and deployed relative to the overriding compressive artery, ligament or bone. For example, a self-expanding or balloon expandable stent may be disposed in a contracted configuration within a sheath. The sheath may include a marker band system, such as described, e.g., in U.S. Pat. No. 8,702,744, that allows directional deployment of the stent under fluoroscopic guidance. In this way, the inventive stent may be positioned and deployed so that a portion of the stent having desired circumferentially differential radial and hoop strength may be aligned against the anatomical feature inducing the venous compression.

Figure 8A:
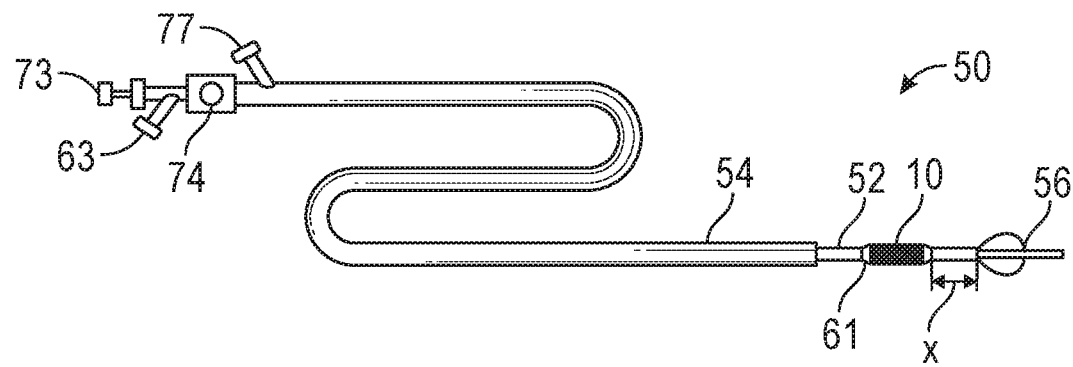
FIGS. 8A-8B are side views of a delivery system for orienting and deploying a stents constructed in accordance with the principles of the present invention.
Figure 8B:
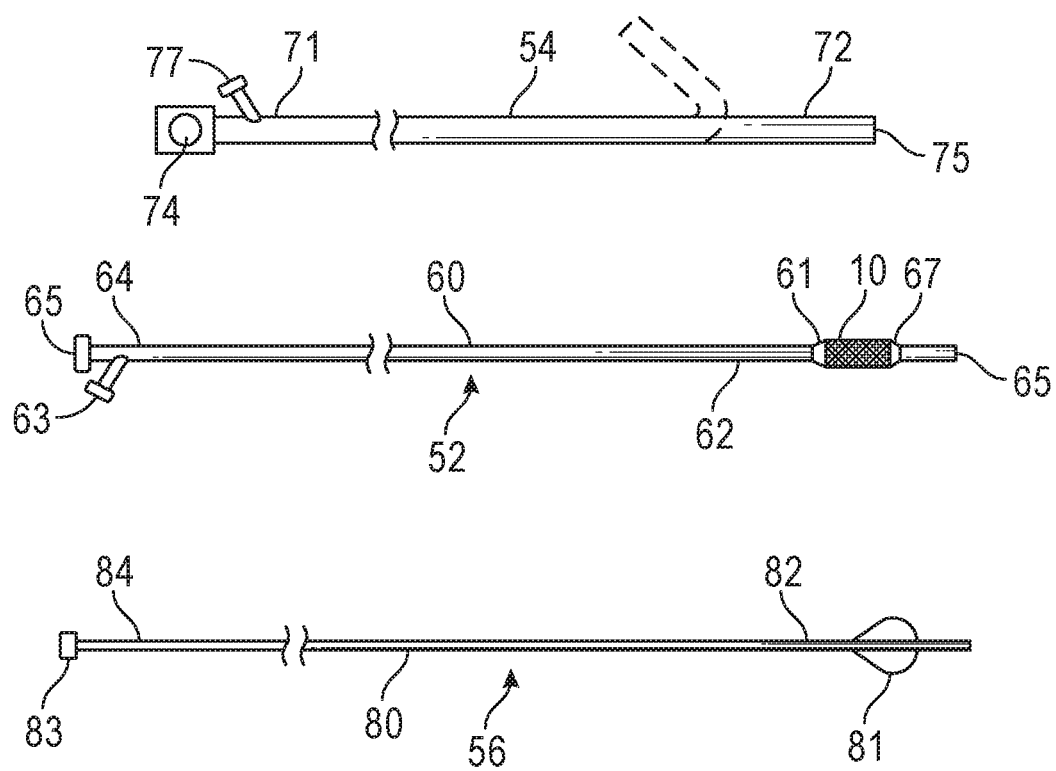

Referring now to FIGS. 8A and 8B, exemplary delivery catheter system 50 suitable for orienting and delivery stents of the present invention is described. Delivery catheter 50 comprises elongated catheter 52, sheath 54, and optional occlusion balloon 56.

Catheter 52 may be of any type appropriate to deliver a suitable stent of the types described hereinabove. For a balloon expandable stent, catheter 52 illustratively includes catheter shaft 60 having balloon 61 disposed in distal region 62 and balloon inflation port 63 disposed on proximal end 64. Inflation port 63 is coupled in fluid communication to the interior of balloon 61 via an inflation lumen. Catheter shaft 60 further includes interior lumen 65 that permits catheter 52 to be advanced over optional occlusion device 56. Stent 10 or 30 may be disposed on balloon 61 for deployment in the iliac vein to counteract the extrinsic compressive load and to restore the patency of the vein. In accordance with one aspect of the present invention, catheter 60 may include pattern 67 of radio-opaque markers that facilitate proper positioning of the catheter and stent within the iliac vein, as described below. Alternatively, if stent 10 or 30 is a self-expanding stent, distal region 62 may omit balloon 61 and instead include a reduced diameter section that accepts the stent in a compressed, contracted state.

Sheath 54 is configured to enclose the stent during transvascular delivery to the region of interest in the iliac vein. Sheath 54 preferably may be formed of a metal braid having a suitable biocompatible covering, e.g., polyurethane, and is configured so that torque applied to the proximal end 71 is accurately reproduced at distal region 72. In this matter, sheath 54 may be rotated using proximal handle 73, to orient distal region 72 (and the enclosed stent) to the proper angular orientation prior to stent deployment. Sheath 54 optionally may comprise articulable distal region that may be adjusted in-situ to position distal region 72 of sheath 54, and distal region 62 of catheter 50 disposed therein, at a selected location within the iliac vein. For example, sheath 54 may include a pull-wire coupled to a point on the circumference of distal region 72, so that retraction of the pull wire causes the distal region of the sheath to deflect (as shown in dotted lines in FIG. 8B), as is known in the art. Proximal end 71 of sheath 54 further comprises control knob 74 coupled to the pull wire to selectively cause distal region 72 to deflect.

Sheath 54 further includes central lumen 75 that permits delivery catheter 60 to be advanced therethrough, and port 77. When catheter 60 is disposed within the central lumen of sheath 54, lumen 75 may form an annulus through which suction may be drawn to aspirate emboli-laden blood through the opening in distal region 72 via port 77. Alternatively, port 77 may be used to infuse a contrast agent to visualize the iliac artery during and following the stent delivery procedure. In addition to catheter 60, or in the alternative, sheath 54 may include in distal region 72 having an array of radiopaque markers with dissimilar shapes, which is employed to angularly orient sheath 54 and catheter 52 under fluoroscopic visualization to facilitate stent orientation and deployment.

Optional occlusion device 56 preferably includes shaft 80 formed of a flexible polymer-covered metal braided tube having inflatable occlusion element 81 disposed adjacent to distal end 82 and inflation port 83 at proximal end 84. Shaft 80 includes an inflation lumen that extends along the length of device 56 to provide fluid communication from proximal end 84 to the interior of occlusion element 81. Occlusion device 56 may be employed to occlude blood flow through the iliac artery during a procedure, prior to stent delivery. In particular, occlusion device 56 first may be inserted into a patient's iliac artery to occlude flow so that the iliac vein may sized, using fluoroscopic visualization, to confirm the length and desired deployed diameter of the stent to be employed to restore patency to the vein. Once an appropriate stent has been selected, either pre-loaded onto catheter 60 and enclosed within sheath 54 or loaded during the procedure, the assembled sheath and catheter may be advanced over shaft 80 of occlusion device 56 in the distal direction until distal region 62 of the catheter is disposed at a desired distance from the proximal shoulder of occlusion element 81.

Figure 9B:
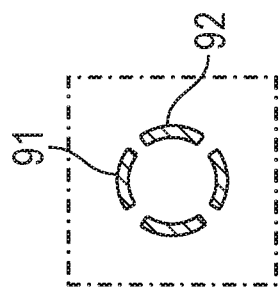
FIGS. 9A-9B are, respectively, a side view of an array of radio-opaque markers for use in positioning the stents of the present invention and an illustrative image of the array of markers when viewed end-on using a fluoroscope.
Figure 9A:
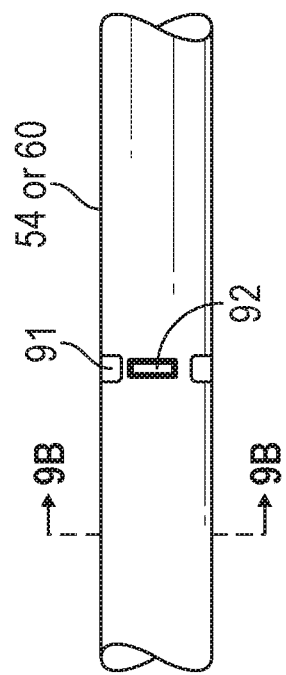

Referring now to FIGS. 9 and 10, exemplary embodiments of delivery catheters having a pattern of radio-opaque markers disposed in its distal region to facilitate stent delivery and orientation using well-known fluoroscopic systems and methods are described. FIGS. 9A and 9B depict a first embodiment of an array of radio-opaque markers having two long markers 91 and two short markers 92, made, e.g., from gold or tantalum, disposed in alternating fashion around the circumference of catheter 60 or sheath 54. Markers 91 and 92 permit the clinician to verify the longitudinal placement of the distal region of the catheter (and correspondingly, the stent) by examining the fluoroscopic image (see FIG. 9B). In addition, variation in the length of the markers around the circumference of the catheter permits the clinician to verify the angular orientation of the catheter and stent prior to stent deployment.

Figure 10B:
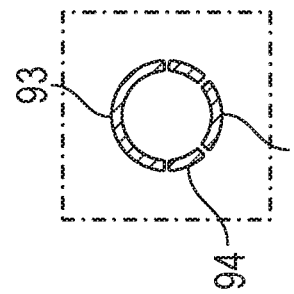
FIGS. 10A-10B are, respectively, a side view of an alternative array of radio-opaque markers for use in positioning the stents of the present invention and an illustrative image of the array of markers when viewed end-on using a fluoroscope.
Figure 10A:
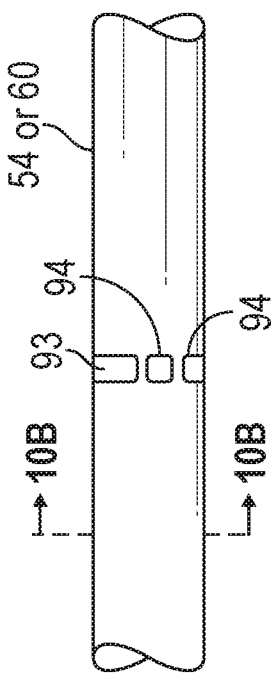

FIGS. 10A and 10B depict an alternative arrangement of markers including a single long marker 93 that spans half of the circumference of the catheter or sheath and three shorter markers 94 disposed on the remainder of the catheter circumference. These markings appear in the corresponding fluoroscopic image as schematically indicated in FIG. 10B. Persons of ordinary skill will appreciate that many other arrangements of radio-opaque markers may be used on delivery catheter 52 to position and orient the stent prior to deployment.

Figure 11:
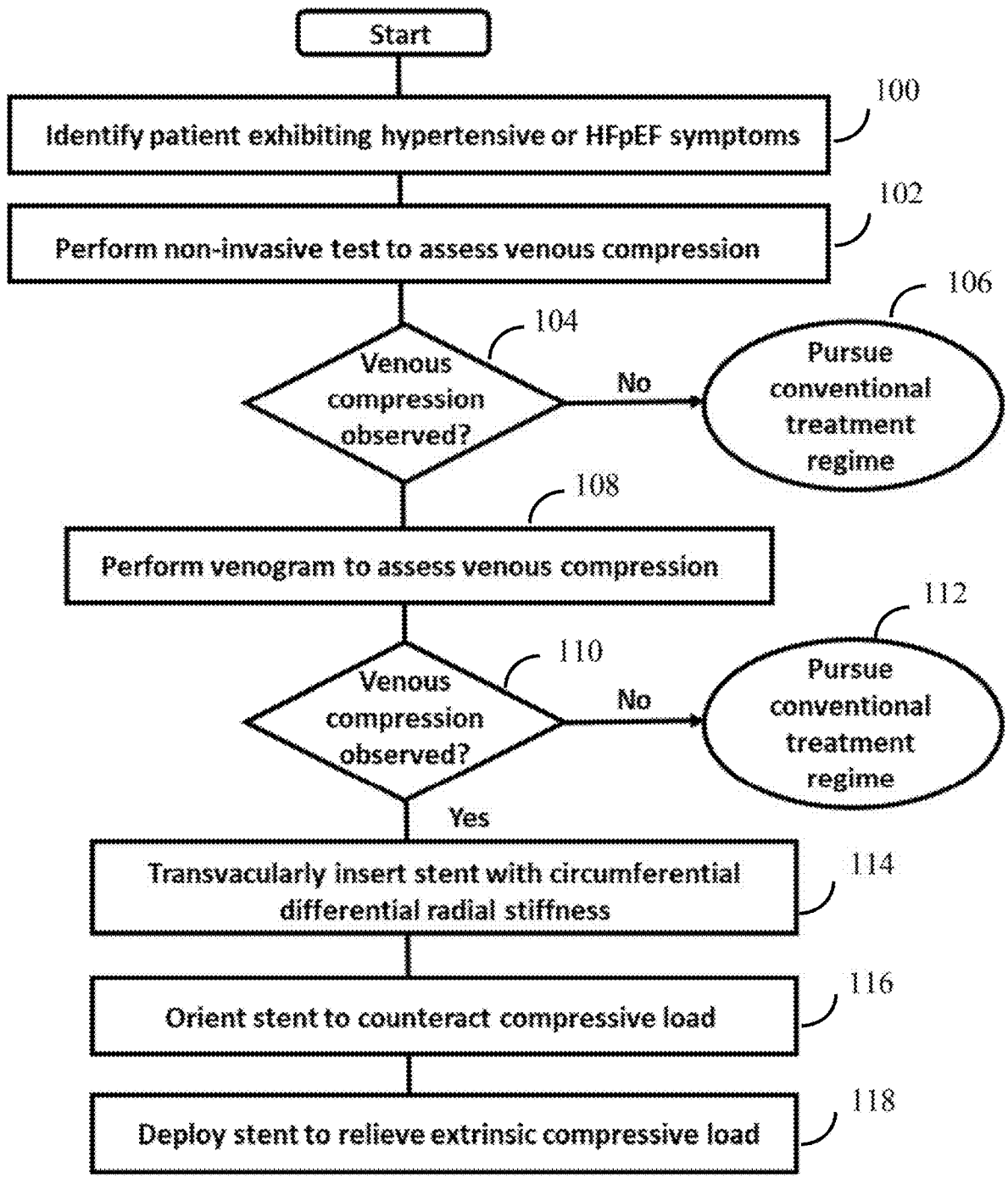
FIG. 11 is an exemplary method of treating a vascular or cardiovascular syndrome by relieving venous compression.

Referring now to FIG. 11, an exemplary method of the present invention is described. As described above, it is the inventor's insight and hypothesis that many hypertensive syndromes may arise due to undiagnosed extrinsic venous compression/obstruction, and that relieving such venous compression/obstruction may ameliorate some or all of the symptoms typically associated with such syndromes. A first step of the method for treating hypertensive syndromes may begin with a patient suspected exhibiting symptoms of hypertension, ISH, MTS or dyspnea being identified, as set forth in step 100. Next, a clinician conducts non-invasive testing, e.g., using a magnetic resonance venography or computed tomographic venography, to assess whether the patient is experiencing venous compression, at step 102, and to assess vein diameter. If the non-invasive scan indicates little or no venous compression of the iliac veins at step 104, a conventional therapeutic regime may be prescribed for the patient at step 106.

However, if at step 104, the non-invasive scan indicates potential extrinsic venous compression/obstruction, the clinician may direct that a more invasive procedure, such as venography, be performed, step 108. If, as a result of the more invasive testing conducted at step 108, the clinician determines at step 110 that the extent of iliac venous compression observed is unlikely to be causing the vascular or cardiovascular symptoms, a conventional therapeutic regime may be prescribed for the patient at step 112. If, however, at step 110, the clinician observes significant iliac venous compression, e.g., more than 10 or 20% reduction in iliac vein diameter, an iliac vein stenting procedure may be prescribed.

Depending upon the suspected cause of the venous compression, i.e., whether an overriding bone or tumorous tissue mass, an open surgical procedure may be required. On the other hand, if the venous compression is attributable to an overriding artery or ligament, including an artery exhibiting age-related reduction in compliance, the clinician may elect to treat the venous compression by implanting a stent configured as described above, at step 114. More specifically, the clinician may determine the native diameter of the compressed iliac vein using a combination of fluoroscopic images and/or by placing optional occlusion catheter 56 in the patient's vein to permit an appropriate stent size to be selected. After the stent is loaded onto a delivery catheter, e.g., as described above with respect to FIGS. 8A and 8B, the stent may be transvascularly delivered into the patient's iliac vein, as set forth at step 114.

Next, at step 116, the handle of the delivery catheter may be rotated angularly to align the portion of the stent having high radial stiffness with the extrinsic localized compressive load. This step may be accomplished using an array of radio-opaque markers disposed on a sheath or catheter of the delivery catheter, as described above. Finally, at step 118, the sheath may be retracted to deploy the stent, if self-expanding, or the balloon of the catheter may be inflated to expand a balloon expandable stent. A contrast agent may be delivered to the iliac vein, for example, using a side port of the sheath, to confirm that the stent is fully deployed and has restored patency to the iliac vein. As discussed throughout this specification, deployment of a stent constructed in accordance with the principles of the present invention, at step 118, is expected to restore patency of the vein and reduce or eliminate the symptoms of the initially identified hypertensive or HFpEF syndrome.

While various illustrative embodiments of the invention are described above, it will be apparent to one skilled in the art that various changes and modifications may be made therein without departing from the invention. For example, as will be understood by a person having ordinary skill in the art, that other configurations could be employed to provide a stent with differential circumferential radial strength, e.g., a braided stent with strands having a stiffness that varies along the length of the strand. Moreover, an exemplary delivery catheter is describes, and persons of skill in the art of catheter design and stent delivery will appreciate that many other delivery catheter designs could be used to deliver and orient the inventive stents. The appended claims are intended to cover all such changes and modifications that fall within the true scope of the invention.

What is claimed:

1. A method of treating heart failure with preserved ejection fraction (HFpEF), May-Thuner Syndrome, or other venous compression/obstruction syndromes, the method comprising the steps of:
   identifying a patient as presenting with symptoms of at least one of heart failure with preserved ejection fraction, May-Thuner Syndrome or a venous compression/obstruction syndrome;
   performing a non-invasive test to assess presence of impaired iliac venous blood flow;
   if the non-invasive test indicates impaired iliac venous blood flow, performing a venogram to identify an area of localized narrowing of a patient's iliac vein;
   transvascularly positioning a stent having a circumferential differential radial stiffness within the patient's iliac vein;
   orienting the stent so that the circumferential differential radial stiffness is aligned with the area of localized narrowing of the patient's iliac vein; and
   deploying the stent within the patient's iliac vein to reduce the localized narrowing of the patient's iliac vein.

2. The method of claim 1, wherein performing a non-invasive test comprises employing either magnetic resonance venography or computed tomographic venography.

3. The method of claim 1, wherein performing a venogram to identify an area of localized narrowing of a patient's iliac vein comprises employing a venogram to determine a circumferential extent of an extrinsic localized compression of the patient's iliac vein.

4. The method of claim 1, further comprising determining a diameter of the patient's iliac artery near the area of localized narrowing of the patient's iliac vein.

5. The method of claim 4, further comprising selecting a stent suitable for use in stenting the area of localized narrowing of the patient's iliac vein, wherein the selection includes selecting a length of the stent and a circumferential differential radial stiffness sufficient to counteract a load causing the extrinsic localized compression of a patient's iliac vein when the stent is deployed.

6. The method of claim 1, further comprising providing a delivery catheter, wherein orienting the stent comprises rotating the delivery catheter.

7. The method of claim 6, wherein providing a delivery catheter comprises providing a delivery catheter having sufficient rigidity to transmit a torque applied at a proximal end of the delivery catheter to a distal end of the delivery catheter.

8. The method of claim 7, further comprising providing a delivery catheter, wherein orienting the stent comprises rotating the delivery catheter.

9. The method of claim 6, wherein the delivery catheter comprises an array of radio-opaque markers configured to facilitate angular orientation of the stent within the patient's iliac vein prior to stent deployment, when viewed under fluoroscopic guidance, such that orienting the stent comprises rotating the delivery catheter under fluoroscopic guidance.

10. The method of claim 1, wherein deploying the stent within the patient's iliac vein comprises either releasing a self-expanding stent or balloon expanding a balloon expandable stent.

* * * * *